US006224379B1

(12) United States Patent
Abedian et al.

(10) Patent No.: US 6,224,379 B1
(45) Date of Patent: May 1, 2001

(54) METHOD FOR SHAPING AN ADHESIVE MATERIAL

(75) Inventors: Behrouz Abedian, Lincoln; Livia M. Racz, Arlington; James P. O'Leary, Medford; Philip L. Millstein, Cambridge, all of MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/165,387

(22) Filed: Oct. 2, 1998

(51) Int. Cl.[7] ....................................... A61C 5/02
(52) U.S. Cl. .............................. 433/224; 433/226
(58) Field of Search ..................... 433/224, 226, 433/81, 102

(56) References Cited

U.S. PATENT DOCUMENTS

| 3,898,739 | 8/1975 | Gayso . | |
|---|---|---|---|
| 4,114,271 | 9/1978 | Howa | ........................................ 32/2 |
| 4,219,619 | 8/1980 | Zarow | .................................. 433/118 |
| 4,283,174 | 8/1981 | Sertich | ................................. 433/119 |
| 4,283,175 | 8/1981 | Nash | .................................... 433/119 |
| 4,345,899 | 8/1982 | Vlock | .................................... 433/165 |
| 4,850,875 | 7/1989 | Takatsu | ................................. 433/226 |
| 4,943,236 | 7/1990 | Linkow et al. | ....................... 433/165 |
| 5,098,298 | * 3/1992 | Johnson | .................................. 433/81 |
| 5,244,933 | 9/1993 | Eidenbenz et al. | ...................... 522/3 |
| 5,277,739 | 1/1994 | Müller et al. | ..................... 156/330.9 |
| 5,302,129 | * 4/1994 | Heath et al. | ............................ 433/81 |
| 5,310,341 | 5/1994 | Byer | ..................................... 433/116 |
| 5,350,298 | * 9/1994 | Delaire | ................................... 433/81 |
| 5,554,030 | 9/1996 | Ario et al. | ........................... 433/226 |

FOREIGN PATENT DOCUMENTS

| 297 20 547 U1 | 11/1997 | (DE) . |
|---|---|---|
| 648487 | 1/1951 | (GB) . |

* cited by examiner

*Primary Examiner*—Ralph A. Lewis
(74) *Attorney, Agent, or Firm*—Hamilton, Brook, Smith & Reynolds, P.C.

(57) ABSTRACT

A spinning end of a rotating instrument is used to deform an adhesive material without the adhesive material adhering to the instrument. This process is particularly suited for packing dental composites within oral cavities.

24 Claims, 2 Drawing Sheets

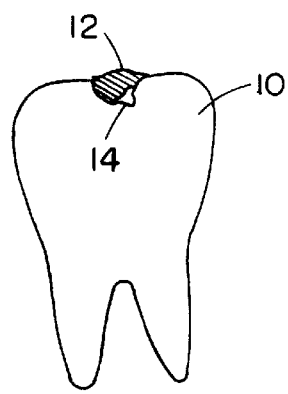
FIG. 1 (PRIOR ART)
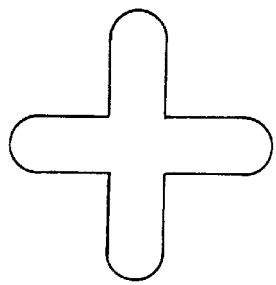 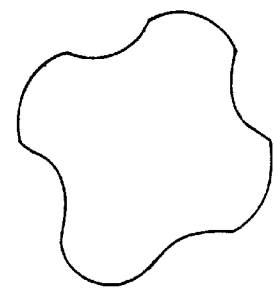 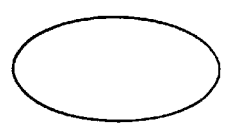
FIG. 2A  FIG. 2B  FIG. 2C
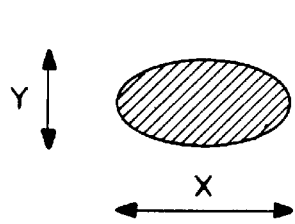 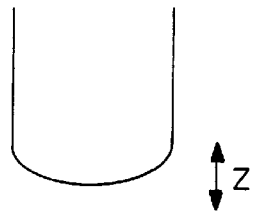
FIG. 3A  FIG. 3B

METHOD FOR SHAPING AN ADHESIVE MATERIAL

BACKGROUND OF THE INVENTION

The field of dentistry routinely requires the manipulation of a high-viscosity, adhesive material. In one application, a dimethacrylate composite is used to fill oral cavities. Dimethacrylate composite esthetic restorative materials have been the subject of considerable research since their introduction in 1962. They represent the current state of the art in the drive to develop restorative materials that have the appearance of natural teeth and do not contain mercury. Composite restorations have been shown to have good clinical performance, particularly for application in the anterior portion of the mouth, where the mechanical stresses to which the restoration is subjected are comparatively low. Posterior, load-bearing applications are generally more problematic. It has been demonstrated, however, that when properly placed, composite dental materials can produce posterior restorations with excellent longevity. Proper placement refers to placement and packing of dental restoratives in such a way that firm adhesion to the dental substructure is achieved, with a minimum number and size of voids due to air entrapment, and minimization of overall porosity.

Due to their strong adhesive properties, composite restorative materials can stick to dental instruments and be difficult to manipulate, causing the practitioner to introduce flaws and voids into a restoration that may cause a degradation of nominal mechanical and clinical properties. During a dental restorative procedure, after a composite is initially placed inside an oral cavity, a step is routinely required in which pressure is applied to the composite to remove entrapped air and to ensure adaptation and a firm bond of the composite to the cavity walls. This step is referred to as "packing," and is fraught with difficulties caused by the extreme stickiness of the restorative materials. In general, the composite sticks to the packing tool when the tool is withdrawn from the restoration. As shown in the illustration of a restored tooth 10 in FIG. 1, the resulting strain on the composite 12 during the removal phase can cause air entrapment and disbanding of the composite 12 from the inner walls 14 of the cavity.

The sticking of the restorative material to the tool is known as adhesion, or adhesive "tack," the elimination of which has been the focus of considerable efforts over the last two decades. Presently, packing tools commonly used by dental practitioners include instruments, or "pluggers," with a variety of geometries made of materials such as plastic, Teflon®, and stainless steel, as well as injection syringes.

The development of low-viscosity, flowable composites have effectively removed the packing step from the clinical procedure. However, in order to achieve low viscosity, these composites are manufactured with a lower volume percentage of filler particles in their matrix, and therefore do not have the mechanical strength of high-viscosity composites. Flowable composites are recommended for small class III or class V cavities, but are not recommended for large cavities or for any application subject to wear.

SUMMARY OF THE INVENTION

The adhesion phenomenon associated with currently-available tools greatly limits the manipulative procedures that can ordinarily be used for packing. This invention provides a new method for effectively packing and placing high-viscosity, wear-resistant, adhesive materials, such as chemically-cured and photopolymerized dental restorative composites, with a significant reduction or elimination of adhesion between the high-viscosity, adhesive material and the packing tool. In accordance with the broad aspects of this invention, the methods are further suited to the deformation of other adhesive materials in applications where deformation without tack is desirable. Examples of such applications include processing involving paint or food.

In a method of this invention, a spinning end of a rotating instrument is used to deform an adhesive material without the adhesive material adhering to the instrument.

In a preferred embodiment, the adhesive material is a dental restorative that is applied to a tooth. Preferably, the adhesive dental restorative is applied to a cavity in the tooth and packed into the cavity with the spinning end of the rotating instrument. The dental restorative is preferably a composite of up to 50% particulate fillers in a copolymer matrix, including a dimethacrylate, for example. One preferred copolymer matrix includes a combination of bisphenol A-glycidyl methacrylate (BIS-GMA) and triethylene glycol dimethacrylate (TEG-DMA). A preferred embodiment of the instrument includes a bit rotated by a motorized, hand-held tool.

Preferably, the adhesive material is in a plastic state. The term, "plastic," as used in its adjective sense, here, means that the material is pliant and capable of being molded. Such a material is at a temperature greater than its glass-transition temperature.

In further preferred embodiments, the instrument is rotated at a rate sufficient to generate a vibrational frequency at least as great as a critical frequency in the adhesive material. The critical frequency is the minimum vibrational frequency at which the adhesive material will not adhere to the instrument. Preferably, the spinning end of the rotating instrument has a smooth, blunted, non-circular shape and is made of a material that will not contaminate the copolymer dental-restorative composite, that material is preferably plastic.

The methods of this invention offer the advantage of a significant reduction or elimination of adhesion between the composite resin and the packing tool. As a result, restorations shaped in accordance with this invention are likely to have improved longevity due to improved placement. Further, the improved properties and greater ease of use of dental resins enables more extensive use of dental resins in dental filling operations. Finally, the ability to manipulate adhesive materials that are considered unworkable by conventional means may enable the practical utilization of new classes of dental resins with improved mechanical and thermophysical properties.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is an illustration of an improperly packed dental restorative filling.

FIGS. 2A, 2B and 2C illustrate various cross-sectional shapes of the ends of instruments for manipulating adhesive material.

FIG. 3A illustrates the cross-sectional shape of the end of an instrument used, as described in the "Experimental" section, to manipulate an adhesive material. The cross-section is taken along a plane perpendicular to the axis of the instrument.

FIG. 3B illustrates the cross-sectional shape of the same instrument that was illustrated in FIG. 3A along the axis of the instrument.

DETAILED DESCRIPTION OF THE INVENTION

Figure 4A:
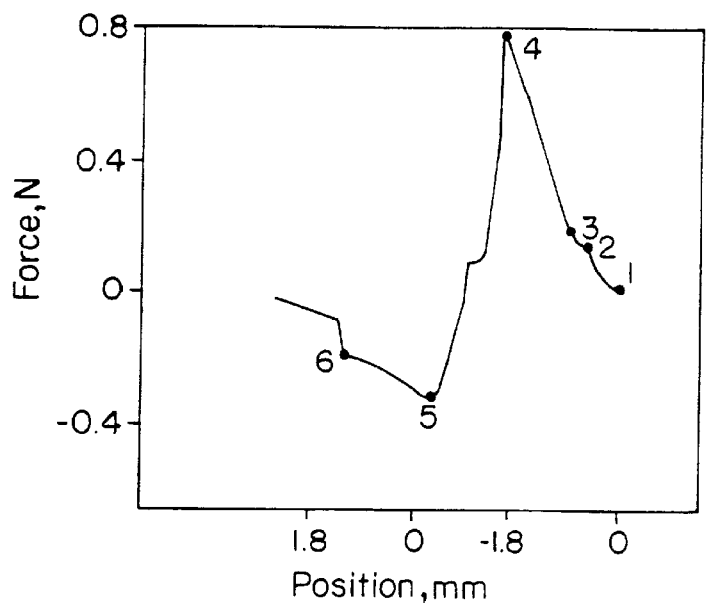
FIG. 4A is a graph illustrating the force exerted on a test bit when inserted into and extracted from an adhesive material without rotation.

The features and other details of the method of the invention will now be more particularly described with reference to the accompanying drawings and pointed out in the claims. Numbers that appear in more than one figure represent the same item. It will be understood that the particular embodiments of the invention are shown by way of illustration and not as limitations of the invention. The principal features of this invention can be employed in various embodiments without departing from the scope of the invention.

One embodiment of an instrument for use with this invention is a bit that can have any of a variety of cross-sectional shapes within certain specifications that are enumerated below. The bit is to be driven by any hand-held, motorized, rotating tool. Such tools are readily available in most dental clinics, but the associated bits are typically used for procedures such as grinding, drilling or sanding. In short, existing bits are designed for reshaping rigid solids, whereas the bit used with this invention is designed for reshaping viscous liquids.

Preferred specifications for the bits of this invention are as follows. The bit is constructed of a non-contaminating material, such as plastic, and may be disposable. Contamination of the adhesive material may occur if the bit is constructed of other materials, particularly metals (such as aluminum), that contaminate by diffusing into the adhesive material and reacting therewith. The avoidance of contamination is particularly important because many of the adhesive materials used in this invention (such as dental restorative composites) can be highly reactive with diffused contaminants. Further, the bit is generally cylindrical along an extended axis about which the bit will rotate. One end of the bit is locked into a rotating tool, which preferably is in the form of a hand-held tool, while the other end is used to mold the composite. Surfaces at the end of the bit that will contact the composite are smooth, with all protrusions being blunt. The cross-sectional geometry at this end of the bit is such that when rotated by a motorized tool, it generates radial oscillations at an interfacial surface of an adhesive, non-flowable material with which it is in contact. Three sample geometries of the end of the bit are illustrated in FIGS. 2A, 2B, and 2C.

In use, the bit is rotated to induce interfacial oscillations in the composite such that the amplitude of the interfacial oscillations are significantly smaller than the bit and cavity diameters. Further, the bit is rotated at a rate that is greater than a critical value. The critical rotation rate is specific to the geometry of the bit and to the material on which it is used. The value of the critical rotation rate for a given system can be readily determined experimentally and catalogued for common materials and geometries.

One example of an adhesive material upon which the methods of this invention can be performed is a composite used for dental applications. The composite includes a copolymer matrix of bisphenol A-glycidyl methacrylate and triethylene glycol dimethacrylate with filler particles of silica and/or zirconia glasses. During a no-tack deformation process, the rotating bit interacts with the interfacial surface of the adhesive material in a way that is mechanically minimal and isothermal. Consequently, the process is not likely to in any way change the chemical structure of the composite. In particular, those properties that are closely linked to the chemistry of the composite, e.g., shrinkage, water sorption, and bond strength will generally not be affected by the no-tack process. The quick action of the bit generates a high-frequency interfacial motion, which is essentially elastic. Because the motion is essentially elastic, no change in mechanical properties of the composite material is expected.

Tacking, which is more specifically defined as the resistance to separation of two materials when they are brought into contact, occurs by one of two mechanisms, cohesion or adhesion. Cohesive tack is defined as the resistance to separation of two materials that stick together due to bulk motion of one or both of the materials. Adhesive tack, on the other hand, is the spontaneous sticking of an adhesive surface to another (non-adhesive) surface under light contact pressures and short durations. Resistance to separation of the two surfaces is predominantly caused by interface dynamics. Adhesive tack describes the mechanism by which pressure-sensitive adhesives stick to solid surfaces, and composite dental restoratives fall into this category.

The degree of tacking can be expressed quantitatively as the total bond energy, $\theta$, dissipated during debonding of a solid-liquid interface. $\theta$ is equal to the reversible work of adsorption, $\theta_0$, times the irreversible work of deformation of the adhesive, H.

$$\theta = \theta_0 H \qquad (1)$$

$\theta_0$ is related to the activation energy per unit area of wetted surface. In the limit of slow rate of change, $$H \to 1 \text{ as } t \to \infty. \qquad (2)$$

For a situation in which pressure-sensitive adhesion is the dominant mechanism, bonding can be prevented by raising the energy required for the solid-fluid interface to form the bond. This can be accomplished by subjecting the fluid at the interface to an oscillatory force. For example, inserting a rotating bit that is non-axisymmetric or has periodic protrusions on its cross-section (see FIGS. 2A–C) meets this criterion.

As the oscillation frequency increases, the rate of strain at the fluid surface increases. For a strain, $\epsilon(t)$, at the fluid surface, the viscoelastic and inertial stresses, expressed as $\tau_{visc}$ and $\tau_{in}$, respectively, are given by $$\tau_{visc} = E_b \epsilon(t) + (\eta_b + \eta_s)\frac{d\epsilon}{dt}, \qquad (3)$$

and $$\tau_{in} = \rho\alpha\frac{d^2\epsilon}{dt^2}, \qquad (4)$$

where $E_b$ is the bulk modulus of elasticity, $\eta_b$ is the bulk viscosity of the viscoelastic fluid and is a function of fluid oscillation frequency, $\eta_s$, represents the surface viscosity, $\rho$ is the fluid density, and $\alpha$ is the length scale that characterizes the deformation of the surface.

Accordingly, the change in energy due to dynamic deformation of the surface becomes $$\Delta E = \frac{1}{2}E_b \varepsilon^2 + (\eta_b + \eta_s)\left(\frac{d\varepsilon}{dt}\right)^2 + \frac{1}{2}\rho a^2 \frac{d}{dt}\left[\left(\frac{d\varepsilon}{dt}\right)^2\right]. \quad (5)$$

If it is assumed that the fluid surface undergoes a periodic sinusoidal deformation, $$\varepsilon = \varepsilon_0 \sin(\omega t), \quad (6)$$

Equation 5 becomes $$|\Delta E| = \frac{1}{2}E_b\varepsilon_0^2 + (\eta_b + \eta_s)\omega^2\varepsilon_0^2 + \frac{1}{2}\rho a^2 \omega^3 \varepsilon_0^2. \quad (7)$$

Equation 7 represents the amount of time-averaged extra energy required for tack to take place, if the fluid surface undergoes a sinusoidal oscillation. Equations 6 and 7 show that increasing the deformation frequency increases the viscoelastic and inertial energies of the fluid at the surface. This leads to the conclusion that there is a critical frequency at which the sum of the viscoelastic and inertial energies of the fluid exceeds the energy available for adsorption at the fluid-solid interface.

EXPERIMENTAL (A) Materials and Methods

The following procedures were performed in order to test the feasibility of a dental instrument based on the concepts described in the previous section. First, a series of cylindrical holes simulating oversized Class-I cavities were hollowed out in a Teflon slab. The holes, which had a diameter of 6.25 mm and a depth of 3.75 mm, were made larger than most actual cavities, for ease of matching and observation.

The slab was then mounted on an inverted tension transducer on an Instron material testing machine. A Dremel tool, which is an all-purpose rotation hand tool able to accommodate a variety of bits, was used to provide the rotation motion. It was mounted on the upper sample holder of the Instron machine.

The geometry of the end of the bit used in the experiments is illustrated in FIGS. 3A–B. The bit is made of polyethylene and has an elliptical cross-sectional shape at its end. The major axis diameter (x) is 2.54 mm, and the minor axis diameter (y) is 1.27 mm. The length (z) of the rounded end of the bit is 1.1 mm. This geometry was achieved by starting with a circular cross-section, slicing off chords opposite one another, and sanding the sharp edges until an ellipse is achieved. This cross-sectional geometry was chosen because it is easy to fabricate and, when rotated in a fluid, it induces the oscillations necessary to test the feasibility of our proposed method.

The flash rate of a strobe light was used to verify the rotation of the bit. The slab with the cavity models was then placed on the inverted tension transducer and aligned so that the bit would depress the composite in the center of the chosen cavity. A commercially-available dental restorative was syringed into the cavity. The tested resins include Perfection® shades A1 and C1, available from DenMat Corporation. Each of these resins has a matrix combination of ethoxylated bisphenol A dimethacrylate and triethylene glycol dimethacrylate and a filler of sub-micron-hydrophobic silica particles. The composition of the resins is more fully described in U.S. Pat. No. 4,859,716.

Side-by-side comparisons of insertion and extraction forces using a rotating vs. non-rotating bit were performed on both resins. In all of the experiments, the composite was applied until it completely filled the cylindrical cavity. The top surface was then leveled off with a Teflon-coated instrument.

The extension cycle of the Instron machine, during which a bit was inserted into and removed from the dental resin, was initiated by a programmed sequence. The bit, in one of three conditions, (a) not rotating (b) rotating at 4100 revolutions per minute (rpm), or (c) rotating at 8500 rpm, was lowered at a rate of 5 cm/minute until it penetrated the composite and continued 1.8 mm below the surface. After a brief pause, the bit was raised out of the composite at a rate of 5 cm/minute, until it reached its original position. The force experienced by the transducer during the course of the cycle was continuously recorded for each experiment, resulting in a series of characteristic curves that allowed for preliminary conclusions about insertion force, extraction force, certain viscoelastic and thermophysical properties, and certain details about the deformation and breakup of the resin free surface.

(B) Results

Experiments were initially performed with a non-rotating bit to simulate the current method of deforming composite dental restoratives. Tests were then performed with a rotating bit. Details of the preliminary investigation are as follows.

Figure 4B:
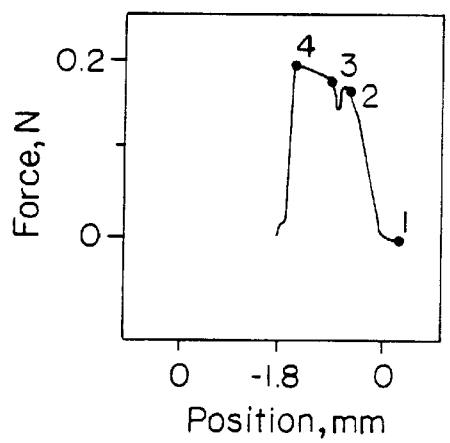
FIG. 4B is a graph illustrating the force exerted on a test bit when inserted into and extracted from an adhesive material with the bit rotating at 4100 rpm.
Figure 4C:
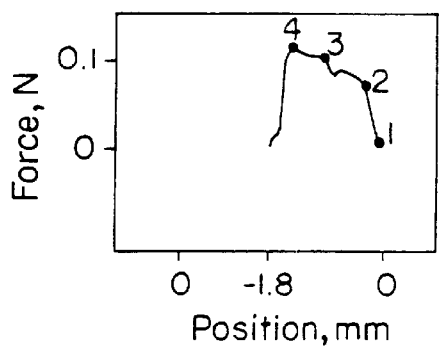
FIG. 4C is a graph illustrating the force exerted on a test bit when inserted into and extracted from an adhesive material with the bit rotating at 8500 rpm.

FIGS. 4A–C show a comparison of representative force vs. distance curves for insertion and extraction of the test bit into material Perfection® A1 under three conditions: (a) non-rotating bit (FIG. 4A), (b) bit rotating at 4100 rpm (FIG. 4B), and (c) bit rotating at 8500 rpm (FIG. 4C). In each of the graphs, the insertion/extraction process is plotted from right to left. The table, below, shows the energy required for insertion and extraction of the test bit under three conditions, non-rotating, rotating and 4100 rpm, and rotating at 8500 rpm, for Perfection® shades A1 and C1.

| Material | Speed (rpm) | Insertion ($10^{-3}$ J) | Extraction ($10^{-3}$ J) |
|---|---|---|---|
| A1 | 0 | 1.519 | 1.844 |
| A1 | 4100 | 0.317 | 0 |
| A1 | 8500 | 0.355 | 0 |
| C1 | 0 | 1.078 | 1.077 |
| C1 | 4200 | 0.143 | 0 |
| C1 | 8500 | 0.141 | 0 |

(C) Discussion—Interpretation of Results

The physical interpretation of the plots shown in FIGS. 4A–C is as follows. In FIG. 4A (non-rotating bit), the insertion portion of the cycle can be divided into two regions. Starting from the far right, the region between points 1 and 2 represents the earliest stage of the insertion cycle, during which the force increases due to deformation of the free surface of the resin. Following this stage, a small notch can be observed in the curve, indicating the point at which the surface of the material under the tip of the bit breaks up. Following the breakup, at point 3, the force increases approximately linearly with distance into the composite, indicating that this is the force required to stretch the interface between the resin and the sides of the bit.

The extraction cycle begins at point 4, where the slope of the force curves shifts direction. After the force plot crosses the x-axis, a negative force builds due to adhesive resistance at the bit-resin interface. Once the curve crosses the 0-mm position on the x-axis, the bit is above the original level of the free surface. At this stage of the experiment, a catenoid of resin material was seen sticking to the bit. At point 5, the magnitude of the force starts to decrease, as the line interface between the resin and the sides of the bit begins to slip. Following point 6, the magnitude of the force abruptly declines near the end of the extraction cycle, which represents detachment of the resin from the bit, and the resettling of the free surface.

It is evident from the curves in FIGS. 4B and 4C and the values in the table that no resistive force was measured in any of the extraction cycles in which the bit was rotating. As in the non-rotating bit test, the region between points 1 and 2 of the insertion cycle is attributed to deformation of the surface in contact with the tip of the bit. As before, this stage is followed by breakup of the resin surface, indicated by the initial notch in the curves. The size of the notch differs among the different resins, and can, in principle, be correlated to the surface tension of the material. Beyond the breakup notch, at point 3, the shape of the curve again is attributed to stretching of the interface between the resin and the sides of the bit. The perturbations in the curves beyond point 3 are in part attributed to the periodic deformation of the resin-bit interface, and in part to the sensitivity of the force transducer to the vibrational motion to which it is subjected.

Upon initiation of the extraction cycle at point 4, during which the bit is removed from the resin, the force returns quickly to zero and remains zero until the cycle is completed. This indicates that there is no measurable resistance to extraction of the rotating bit at either of the two rotation rates at which tests were done. The qualitative characteristics of the curves in FIGS. 4B and 4C are comparable, but the amplitude of the curve, and therefore the insertion force, is lower at the higher rotation rate. This suggests that the level of tactile response that an operator obtains from a composite depends on the rate of rotation of his hand tool. In order to obtain the maximum packing force, for example, one would operate at the lowest speed at which tacking energy is overcome. The critical rotation rate for the test systems (i.e., the rotational rate at which the instrument will generate a critical-frequency vibration in the resin) could not be determined, as it was below 4100 rpm, which was the lowest rotation rate at which the apparatus would operate. One could, with a continuously-variable motor, readily obtain the critical rotation rate for any system by empirical methods.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for shaping an adhesive material, comprising the steps of:
   filling a cavity with a pressure-sensitive adhesive material that is in a plastic state;
   rotating an instrument about an axis;
   contacting the plastic pressure-sensitive adhesive material with a spinning end of the rotating instrument after the cavity is filled with the plastic pressure-sensitive adhesive material; and
   deforming the pressure-sensitive adhesive material with the spinning end of the rotating instrument without the pressure-sensitive adhesive material adhering to the spinning end.

2. The method of claim 1, wherein the rotating instrument generates a vibration in the adhesive material, the vibration having a frequency equal to or greater than a critical frequency, below which the adhesive material would adhere to the instrument.

3. The method of claim 2, further comprising the step of filling a cavity with the adhesive material before the adhesive material is deformed by the spinning end of the rotating instrument.

4. The method of claim 3, wherein the spinning end of the rotating instrument is used to pack the adhesive material.

5. The method of claim 4, wherein the adhesive material is packed with the spinning end of a rotating bit.

6. The method of claim 5, wherein the spinning end of the rotating bit has a noncircular shape in a plane normal to its rotating axis.

7. The method of claim 6, wherein the spinning end of the rotating bit is smooth and any protrusions at the spinning end are blunted.

8. The method of claim 7, wherein the spinning end of the rotating bit does not contaminate the adhesive material.

9. The method of claim 8, wherein the spinning end of the rotating bit is made of plastic.

10. A method for performing an aesthetic dental surface restoration comprising the steps of:
    applying the adhesive dental restorative to a cavity in a crown of a tooth;
    contacting the adhesive material with a spinning end of a rotating instrument, wherein the adhesive dental restorative is in a plastic state when contacted; and
    manipulating the adhesive dental restorative with the spinning end of the rotating instrument without the adhesive dental restorative adhering to the spinning end.

11. The method of claim 10, wherein the adhesive dental restorative is applied to a cavity in a tooth.

12. The method of claim 11, wherein the spinning end of the rotating instrument is used to pack the adhesive dental restorative into the cavity in the tooth.

13. The method of claim 12, wherein the rotating instrument generates a vibration in the dental restorative, the vibration having a frequency equal to or greater than a critical frequency, below which the adhesive dental restorative would normally adhere to the instrument.

14. The method of claim 13, wherein the spinning end of the rotating instrument has a noncircular shape in a plane normal to its rotating axis.

15. The method of claim 14, wherein the spinning end of the rotating instrument is smooth and any protrusions at the spinning end are blunted.

16. The method of claim 15, wherein the instrument is a bit rotated by a motorized, hand-held tool.

17. The method of claim 16, wherein the adhesive dental restorative is a composite having a copolymer matrix.

18. The method of claim 17, wherein the adhesive dental restorative includes BIS-GMA and TEG-DMA.

19. The method of claim 18, wherein the spinning end of the rotating instrument is made of plastic.

20. A method for packing an adhesive material in a cavity, comprising the steps of:
    rotating a tool about an axis, wherein the tool has a non-circular shape at an end used for packing; and
    in a substantially isothermal process, packing the adhesive material with the non-circularly-shaped end of the rotating tool, the tool rotating at a rate greater than a critical rotation rate to avoid adherence of the adhesive material to the tool.

21. The method of claim 20, wherein the adhesive material is a dimethacrylate composite aesthetic restorative material.

22. The method of claim 21, wherein the dimethacrylate composite aesthetic restorative material forms a surface restoration on a tooth.

23. The method of claim 20, wherein the tool includes a plastic bit that is used to pack the adhesive material.

24. The method of claim 20, wherein the chemical structure of the adhesive material remains substantially unchanged throughout the packing method.

* * * * *